United States Patent [19]
Duret

[11] Patent Number: 5,092,022
[45] Date of Patent: Mar. 3, 1992

[54] METHOD OF PRODUCING A DENTAL PROSTHESIS

[76] Inventor: François Duret, Rue Paul Claudel, Les Grands Lemps (Isere), France

[21] Appl. No.: 77,012

[22] Filed: Jul. 23, 1987

Related U.S. Application Data

[63] Continuation of Ser. No. 556,435, Nov. 30, 1983, abandoned.

[30] Foreign Application Priority Data

Nov. 30, 1982 [FR] France .................. 82 20349

[51] Int. Cl.$^5$ .......................................... E21F 43/00
[52] U.S. Cl. ............................ 29/160.6; 433/25; 433/213; 364/474.05
[58] Field of Search ............. 29/160.6; 433/25, 213; 364/474

[56] References Cited

U.S. PATENT DOCUMENTS

| | | | |
|---|---|---|---|
| 2,635,338 | 4/1953 | Dallenbach | 29/160.6 |
| 2,774,141 | 12/1956 | Quinn | 29/160.6 |
| 3,861,044 | 1/1975 | Swinson, Jr. | 322/213 |
| 4,324,546 | 4/1982 | Heitlinger | 433/213 |
| 4,575,805 | 3/1986 | Moermann et al. | 433/55 |

Primary Examiner—P. W. Echols
Attorney, Agent, or Firm—Herbert Dubno

[57] ABSTRACT

After the shape of the zone of implantation in the mouth is obtained by direct impression, micro-sensing or optical impression, a prosthesis or a mold for making a prosthesis is automatically machined by machine tool at a work center with the assistance of a calculator or computer which takes into consideration the shape obtained, the material or materials which are to be shaped, and other parameters such as thicknesses and the like which are essential to the proper shape and configuration of the prosthesis which is thus fabricated. The prosthesis can be a crown, bridge or part or assembly of both.

17 Claims, 5 Drawing Sheets

FIG_19

FIG_20

FIG_21

FIG_22

FIG_23

FIG_24

FIG_25

FIG_29

FIG. 31

METHOD OF PRODUCING A DENTAL PROSTHESIS

CROSS REFERENCE TO RELATED APPLICATIONS

This is a continuation of co-pending application Ser. No. 556,435 filed on 30 Nov. 1983, now abandoned.

This application is related to the commonly assigned copending applications Ser. No. 262,905 filed 12 May 1981 by Francois Duret and Christian Termoz (replaced by Ser. No. 580,776 filed 21 Feb. 1984, both now abandoned) and Ser. No. 485,059 filed 14 Apr. 1983 by Francois Duret, Christian Termoz and Elisabeth Duret (now U.S. Pat. No. 4,611,288). Reference may be had to the documents cited in the files of these applications and to the French patent documents upon which they are based and to French application 82 20349 filed 30 Nov. 1982.

FIELD OF THE INVENTION

The present invention relates to a method of producing a dental prosthesis and, more particularly, to the production of permanent, partially fixed and mobile (removable) or complete prostheses.

BACKGROUND OF THE INVENTION

The production of a dental prosthesis customarily requires the following operations:
casting of an impression;
checking the occlusion after production of a model;
mounting on wax for esthetic review;
fabrication of the metal or resin parts by the lost-wax technique;
checking and polishing; and
introducing the prosthesis into the mouth.

This method, which is very old, has a number of disadvantages including:
the need to work in the mouth;
delays at least in part caused by the need to transmit materials and information between the dental technician and the dentist and the time required for the various fabrication steps;
the precision of the fabrication is directly related to the skill of the prosthetist;
the possibility of a disagreement or lack of communication between the prosthetist and the dentist;
high cost because of the large amount of manual labor;
the dependence upon materials which can be used in the lost-wax process; and
the large number of invasive procedures required in the mouth of the patient which are time-consuming and may be even painful and uncomfortable for the patient.

In application Ser. No. 262,905 there is described a method of producing dental prostheses, especially crowns, wherein, after basic preparation of the stump, an interferometric impression is taken of the implantation zone and the resulting interferogram is subjected to an analog/numerical conversion to produce binary data which is combined with stored data to produce numerical control data. This latter data is ultimately used for the numerical control of a machine tool by which the crown is machined.

Application Ser. No. 485,059 (U.S. Pat. No. 4,611,288) discloses further refinements of these principles, especially having reference to the taking of "optical impressions" of the implantation zone or the oral cavity or pertinent parts thereof, and the use of these impressions for automatically or semiautomatically producing a dental prosthesis. The means for taking such optical impressions and for converting them and appropriate stored data to numerical-control signals are likewise described. Applications Ser. No. 262,905 and Ser. No. 485,059 are hereby incorporated by reference in their entireties.

The method described in the Ser. No. 485,059 comprises preparing a dental region in the mouth of a patient to receive a dental prosthesis including at least one prosthetic tooth, directing nontraumatic waves at this region, collecting reflected waves from this region and converting the reflected waves into numerical information signals representing the shape and dimensions of this region. The mouth of the patient is then scanned to establish at least one plane representing an occlusal surface and planes tangent to a prosthesis to be formed at this region in accordance with the shape of the mouth, existing dentition and maxillary movements.

A prosthesis blank is then selected based upon color and is shaped to form the envelope of the prosthetic tooth based upon these predetermined planes. A prosthesis support is automatically machined based upon the numerical information under numerical control so that the support precisely will fit the mouth region.

The blank is secured to the support to form the prosthesis which is then inserted into the mouth of the patient.

OBJECT OF THE INVENTION

It is the principal object of the invention to overcome the drawbacks of earlier methods of fabricating dental prostheses.

Another object of this invention is to extend the principles of U.S. patent application Ser. No. 485,059 (U.S. Pat. No. 4,611,288).

Still another object of the present invention is to provide an improved method of making dental prosthesis either by the direct machining of them or of molds for making same which goes beyond the latter applications and improves upon the techniques disclosed and claimed therein.

SUMMARY OF THE INVENTION

This object is attained, in accordance with the invention, by a process in which the shape of a zone of implantation of the buccal cavity is ascertained by direct impression, by a microsensing (micropalpation) or optical impression technique, and the prosthetic piece itself, a blank for the prosthetic piece or a mold adapted to fabricate the prosthetic piece is formed at a work center with the assistance of a calculator or computer taking into consideration the ascertained shape and the material or materials from which the prosthesis is to be fabricated.

According to one mode of operation, when the prosthesis is to be assembled of a plurality of elements such as in a movable prosthesis or a bridge the shape-determining step consists of determining the shape of the part of the prosthesis which is to lie against the gum and taking into account the relationship between the three known parameters, namely, the surfaces of the two ends of the prosthesis and the low point for a bridge or the support profile for a movable prosthetic device.

It is also important to take into consideration the axis of insertion of the teeth.

According to a feature of the invention, the positioning of the teeth, which comprise the prosthesis over the length of the arcade, is determined and proximal planes are established which are each perpendicular to the line joining two points of contact between the theoretical teeth and/or the line joining the points of contact between the theoretical teeth and the remaining teeth or the line joining the points of contact with the remaining teeth, the number of such planes being a function of the length of the arcade and the number of teeth of the prosthesis. To achieve the final envelope the prosthesis formed as a result of such calculations may be deformed.

In the case of a bridge or removable prosthesis of significant length, the prosthesis or arcade may be subdivided into a number of linear or arcuate sections, the arcuate sections having a large radius of curvature, the subdivision taking into account the angle of attack of the machining tool, with each section being then machined and being joined to the adjacent section or sections by interfitting elements, including a tenon on one section which can engage in recess on the adjoining section.

When a removable prosthesis is fabricated according to the invention, the calculator or computer can be utilized to fabricate a mold in which the plate of this prosthesis is shaped. Thus, for example, one or more parts of the mold may be machined automatically under the control of the calculator or computer and, in this case, the part machined should correspond to the shape of the implantation zone previously described. The shaped part of the mold can thus take into consideration the ascertained shape of the implantation zone, relationships bearing upon the axis of the insertion of the teeth, biochemical calculations necessary for stability of the apparatus, and data such as the zones of pressure with respect to the more sensitive buccal regions and the hooks for securing the prosthesis to adjacent teeth.

The impression of the zone of implementation can be taken either by the method described in Ser. No. 262,905 or that described in Ser. No. 485,059 (U.S. Pat. No. 4,611,288).

When a single support plate is provided, a tooth or a series of teeth which have been fabricated are withdrawn from stock and can be affixed manually or automatically.

The two parts of the mold can be fabricated so that the one defines the ascertained shape of the zone of implantation while the other is composed of a rigid material and defines the shape of the teeth. In this case, a resin can be injected into the mold cavity thus produced to form both the bridge and the plate. A metal can also be so injection molded or die cast.

One of the two parts of the mold, which can be machined automatically in the manner described, can be composed of a deformable material which is provided with cavities into which transformed or prefabricated teeth can be inserted so that these teeth are resiliently held in place. This body of yieldable material can be supported by a rigid cap against the injection pressure and the material for forming the plate can be injected into the mold cavity which is thus formed to simultaneously provide the plate and the interconnections with the teeth. The teeth after molding of the plate can then be withdrawn from the yieldable material of the mold part in which the teeth were previously captured.

According to another feature of the invention, therefore, the mold which is produced by automatic machining utilizing the output of the calculator or computer can be utilized to stamp the support plate for the teeth between the two parts of the mold. Subsequently the stamped plate is finished by a cutting operation utilizing machining, electron bombardment (electron beam machining). Numerically controlled machining (see Ser. No. 485,059, U.S. Pat. No. 4,611,288) can be used.

It is possible in the fabrication of this mold to machine only the part of the mold which corresponds to the impression zone in accordance with the ascertained shape and hence to automatically machine in response to calculator or computer that part which rests against the portion of the gums. The other mold member can be machined taking into consideration the thickness of the material to be stamped and its flow characteristics, based upon the first shape. After machining the countermember, the plate can be stamped and then cut out as previously described.

Various machining techniques can be utilized for fabricating the mold or the plate itself and these machining techniques can include milling, turning, electro-erosion (electric discharge machining), electrochemical machining, ultrasonic machining or laser beam or electron beam machining. Numerical control can be used for whatever machining technique is utilized.

In the case where a crown is to be provided with an aesthetic inlay coating or insert, the crown and the facing can be machined separately and then the facing member can be secured to the crown. During the machining of the crown, of course, the thickness of the facing material, the system for affixing the facing member on the crown itself, the type of inclusion and the like may all be taken into consideration and can be preprogrammed or otherwise considered in the calculations.

The fixing system in each case, however, can include a tenon and one of the two members to be attached which can engage in an undercut recess of the other member.

Alternatively, the facing member can be shaped to the final form after having been attached to the crown.

BRIEF DESCRIPTION OF THE DRAWING

The above and other objects, features and advantages of the present invention will become more readily apparent from the following description, reference being made to the accompanying highly diagrammatic drawing in which.

SPECIFIC DESCRIPTION

Figure 1:
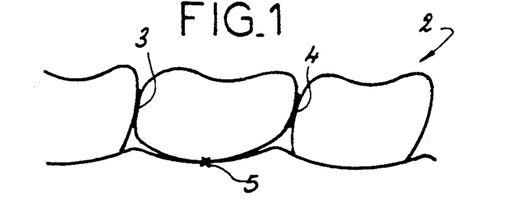
FIG. 1 is a side elevational view diagrammatically illustrating the relationship of critical points in the fabrication of a dental prosthesis according to the invention, schematically illustrating the points of contact between adjacent teeth and the gum line.

In FIG. 1 of the drawing, there is shown a bridge 2 which illustrates the critical surfaces 3 and 4 representing the two extremities of the prosthesis and the low point 5 along the gum line which must be considered in designing a prosthesis device, in this case a replacement tooth to fit between the existing teeth of the mouth.

Figure 2:
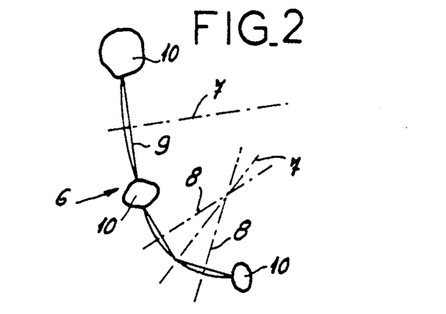
FIG. 2 is a plan view illustrating diagrammatically the positions of remaining teeth where the spaces between them are to be filled with teeth of a dental prosthesis, especially a dental plate.

As can be seen from FIG. 2, after the configuration of the implantation zone has been ascertained and the machining action is to be carried out based upon the calculator or computer values at the fabrication location, where the computer takes into consideration the shape and the material or materials of the member to be machined or to be fabricated in the machine member when the machine element is a mold or a part thereof (see Ser. No. 485,059 U.S. Pat. No. 4,611,288). It is also important in calculating the machining operation to take into consideration the overall appearance of the arcade 6. Only then can one determined the proximal planes 7 and 8, each proximal plane 7 being defined as a plane perpendicular to a line 9 connecting two contact points of the prosthesis with the teeth 10 remaining in the mouth. Each proximal plane 8 is defined as the plane perpendicular to the line connecting a point of contact to another proximal plane.

Figure 3:
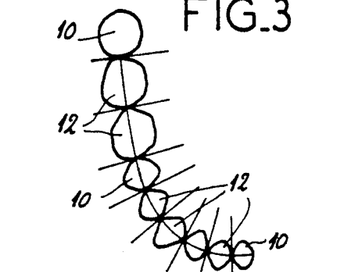
FIG. 3 is a plan view showing the layout of groups of teeth of a dental prosthesis.

After determining the proximal planes, the method of the invention places theoretical teeth 12 along the arcade and possibly subjecting the lay-out to a deformation to modify the envelope to the proper shape as shown diagrammatically in FIG. 3.

Figure 4:
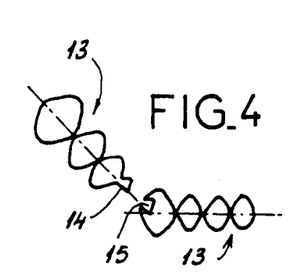
FIGS. 4 and 5 are similar views of the formation of a prosthesis in which two sections are to be joined together by a tenon connection.
Figure 5:
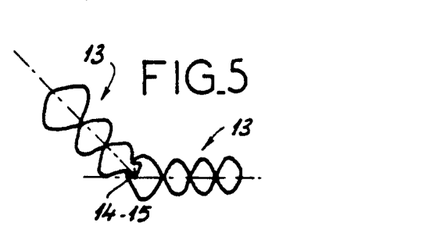

As illustrated in FIGS. 4 and 5, it has been found to be desirable when the arcade or prosthesis is of substantial length, to subdivide the arcade into sections and to assemble the arcade from the plurality of sections 13, for example which may be linear or arcuate and of a large radius of curvature as shown.

Each section can be fabricated separately utilizing the principles of this invention and the sections can be joined by fixing means 14 and 15 here represented as a tenon 14 which is complementary to and fits within a recess 15 utilizing a dovetail connection as shown alone or with a dental cement.

The connection can be made in the region of the central element or substantially midway along the length of the arcade where the curvature is more or less regular.

The cutting of an arcade into a number of sections is effected taking into consideration the angle of attach of the machining tool to ensure that it will be able to operate under the best possible conditions so that, according to the principles of this invention, the tool may be a triaxial tool, i.e. with freedom of control displacement about three axes or at most about four axes and more complex machining devices such as a five-axis tool can be avoided.

According to a feature of the invention, especially for a removable prosthesis, the process comprises forming the two parts of the mold so that they are able to produce between them a support plate for the teeth.

These two mold parts can be fabricated by automatic machining, starting from the ascertained shape of the zone of implantation of the prosthesis and from the relationship which results after taking into consideration the axis of insertion of the teeth, any biomechanical calculation for stability of the appliance, zones of pressure with respect to tender areas of the mouth and the attachment hooks of the prosthesis which enable it to be anchored to adjacent teeth. The information for the logical operation of the computer in consideration of these parameters can all be preprogrammed by any conventional programming means.

In a first embodiment of this respect of the invention, a single support plate can be fabricated and the teeth or a series of prefabricated teeth can be affixed manually or automatically to this support plate taking into consideration the constraints previously indicated.

Figure 6:
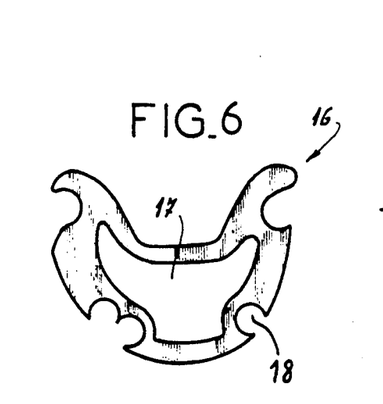
FIG. 6 is a plan view of a support plate for a dental prosthesis prior to the attachment of prefabricated teeth thereto.

In FIG. 6 of the drawing, for example, a plate 16 has been shown which comprises a central opening 17 and peripheral cut-outs 18 provided to accommodate the remaining teeth of the mouth.

Figure 7:
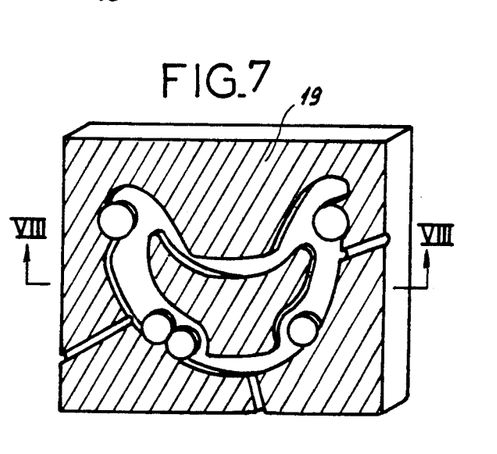
FIG. 7 is a perspective view in section through a female portion of a mold for fabricating such a plate.
Figure 8:
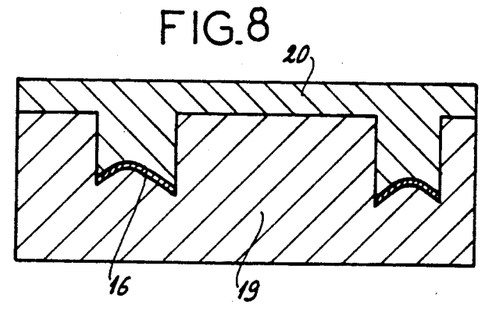
FIG. 8 is a section taken along the line VIII—VIII of FIG. 7 showing the two-mold members in place in the fabrication of the plate.

As shown in FIG. 7, this plate 16 can be stamped by or cast in a mold whose female mold member 19 is sectioned to enable the profile of the plate 16 to be viewed. After closure of the mold, as shown in FIG. 8, the material designed to form the plate 16 can be introduced in a flowable form into the mold cavity for casting or injection. This material can be a synthetic resin or a metal of the type commonly used to form a dental prosthesis.

Figure 9:
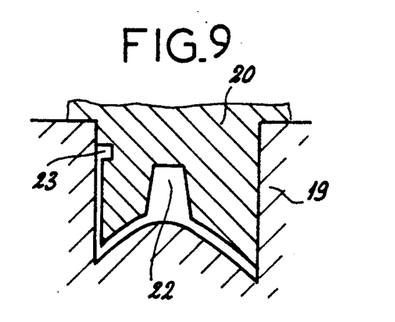
FIG. 9 is a section through another mold illustrating a feature of another aspect of this invention.

It should be clear, especially from FIGS. 8 and 9, that the logic or memory of the calculator or computer can be programmed to take into consideration, during the fabrication of the two parts 19 and 20 of the mold, the thickness of the plate 16 which is obtained and may even be such as to form, as shown in FIG. 9, recesses 22 and 23 in the mold member 20, for example, which result in the production of a tenon, adapted to receive a tooth, and a hook adapted to enable the connection of the prosthesis to adjacent teeth respectively.

Figure 10:
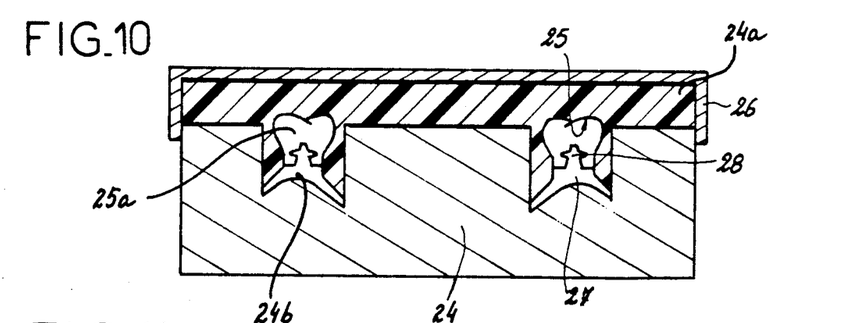
FIG. 10 is a section similar to FIG. 8 wherein, however, the plate is to be formed by injection molding and to be bonded to the teeth previously esconced in the upper mold member.

In the embodiment of FIG. 10, by contrast, the female mold member 24, which may be machined from metal, can cooperate with a female mold member 24a automatically machined from a somewhat yieldable material and which may be made from rubber or an elastomeric plastic and which is provided with cavities 25 adapted to yieldably receive and grip the teeth 25a which can be pressed into these cavities. The surface 24b of the mold member 24 respresents the surface of implantation previously ascertained by any of the means described, e.g. impression by a soft material, microsensing or optical sensing (e.g. as in U.S. Pat. No. 3,861,044 or, more preferably, by the method of Ser. No. 485,059.

In this embodiment of the method of the invention, each prefabricated tooth 25a is inserted into a respective recess 25, the selected prefabricated teeth having profiles which take into consideration the envelope of the prosthesis, the occlusion and the axis of insertion. After closing of the mold, the yieldable part 24a is inserted into a rigid cap 26 preventing displacement of this mold part during injection and the material for the support plate is then injected into the cavity 27 which has the configuration of this plate, this flowable material penetrating into the undercut zones 28 which were present in the prefabricated teeth 25a to form anchorages retaining these teeth upon the plate thus formed. When the plate is removed from the female portion 24 of the mold, the cap 26 can be removed and the teeth attached to the plate can be pulled out of the yieldable member 24a.

According to another embodiment of the invention, the two parts of a mold are fabricated by an automatic machining technique and then used to stamp the support plate between the male and female parts of the mold thereby imparting the general shape to the support plate. The support plate is then finished by a cutting operation, e.g. by a milling, electron bombardment machining, laser beam machining or electro-erosion, preferably under numerical control.

Figure 11:
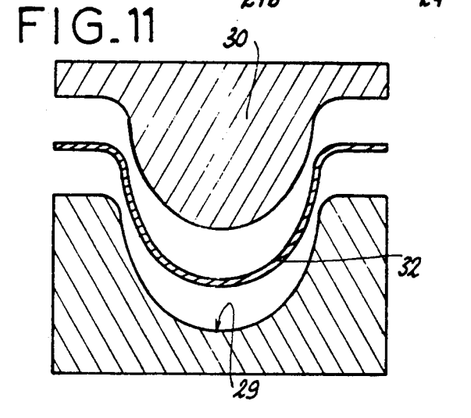
FIG. 11 is a sectional view diagrammatically illustrating the stamping of a support plate according to the invention.
Figure 12:
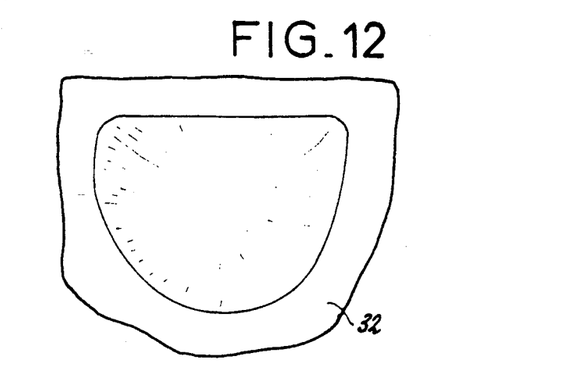
FIG. 12 is a plan view illustrating this plate after stamping and before cutting.
Figure 13:
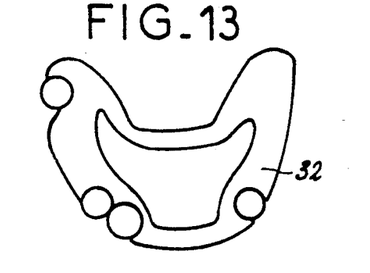
FIG. 13 represents the plate subsequent to cutting, also in a somewhat diagrammatic plan view.

Advantageously, as shown in FIGS. 11 through 13, the region 29 of the female mold part is initially machined to correspond to the zone of impression as ascertained from the gums and to define the region of the pellet or lingual zone. Thereafter, using automatic machining techniques, the male part 30 is machined taking into consideration characteristics of the support plate to be formed, namely, the thickness of the plate, the flow characteristics of the metal or synthetic resin to constitute the plate, and only then is the support plate stamped.

The automatic machining of the second or male part 30 can be effected by the same techniques utilized in the coating of the plate, e.g. by milling, electron beam or laser beam machining or electro-erosion.

The instructions to the numerically controlled machining tool for the machining program of the second part of the mold, suitably adjusted to take into consideration the thickness of the support plate, the material thereof and its flow characteristics, may be derived from the mold constituted by the impression zone contour 29.

As shown in FIGS. 11 and 12, the support plate 32 can then be stamped between the mold parts, and the stamped blank of FIG. 12 can be cut along traces which are determined by taking into consideration the zones at which this plate is to engage the mouth portions, i.e. taking into consideration the seating zones within the mouth.

This means also that the cutting operation should leave concavities for the existing teeth and should also provide, if desired, means such as hooks for retaining the plate in the mouth.

If the hooks are not provided in the cutting operation, they or other fixing means can be formed in a subsequent operation, e.g. by stamping, brazing, adhesive bonding, soldering or welding, and the prefabricated tooth can then be applied, e.g. by soldering, adhesive bonding, screw connection or by any other convenient and conventional mounting method.

It should be noted that the various parts of the mold or of the support plate, to the extent that they are machined, can be fabricated by known machining techniques, such as milling, turning, electro-erosion, electro-chemical machining, electrosonic machining or by bombardment with laser beams or electron beams using the numerical control described in Ser. No. 485,059.

In all of the cases described, the teeth or series of teeth to be fixed to the support plate are stocked and classified or numbered as a function of their shape and their color. They are ordered and oriented on the support plate as a function of the ascertained form, envelope, occlusion and axis of insertion so as to minimize the amount of machining which is possible.

Figure 14:
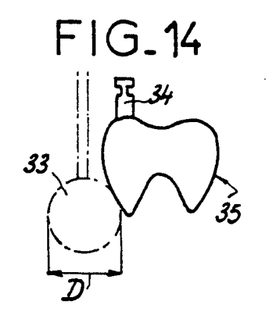
FIG. 14 is a diagrammatic elevational view and FIG. 15 is a diagrammatic top view, illustrating the milling of a crown.

In cases in which the teeth or portions thereof must be machined or machining or parts of the mold, support plate or attachments thereto may be required, a milling tool 33 may be used as shown in FIG. 14 in the case of the shaping of a crown. Here the milling tool 33 can be seen to have a diameter D at the working portion or end of the milling tool which is at least equal to twice the greatest depth of the cut, i.e. twice the thickness of the layer to be removed from the workpiece during the milling operation. This permits the tool to be move relative to the workpiece with only three axes of freedom so that more complex machining tools such as five-axis machining tools (or more complicated ones) need not be employed. At most, the machining tool should be a four-axis machining tool.

Figure 15:
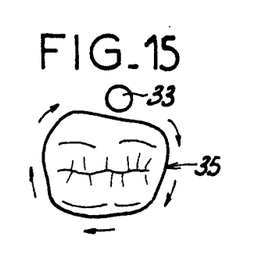
Figure 16:
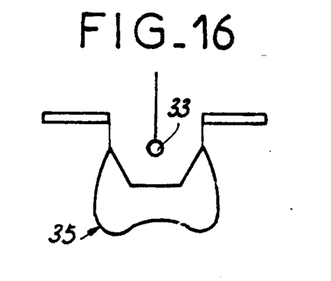
FIG. 16 is a further diagram of the machining of a crown.

In a first operation, the element to be machined can be fixed to a support, e.g. the support 34 which holds the crown 35 while the external face of this prosthesis is machined by an axial displacement of the milling cutter 33 and by its displacement around the prosthesis as represented in FIG. 15. Then the workpiece is turned and the interior can be milled as shown in FIG. 16, the milling of the grooves being effected by a special milling cutter which can be described as a fissure miller. After the machining of the prosthesis is completed and before polishing, supprt 34 can be removed by a cutting operation and the prosthesis is then polished.

This process can be utilized also for producing crowns having aesthetic inserts or facings.

Figures 17, 18:
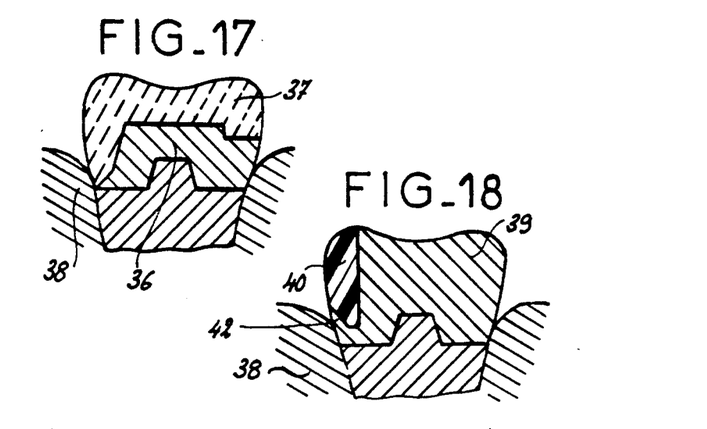
FIGS. 17 and 18 are diagrammatic sections illustrating the formation of ceramo-metallic composite crowns.

For example, in FIG. 17 there is shown an embodiment in which a ceramo-metallic material constitutes the visible portion of a tooth whereas in FIG. 18, a synthetic resin member is inlaid in a metallic crown to form the directly visible portion thereof.

The constraints which must be taken into consideration in the two cases by the machining parameters generated by the calculator or computer are not the same.

For example, in the case where the crown comprises a metallic part 36 which constitutes the base and is fitted thereto the stump of the tooth, the ceramic part 37 can extend into contact with the gum 38.

Howerver, when the metalic part 39 (FIG. 18) is provided with an inlay 30 of synthetic resin, it is desirable to separate the synthetic resin from the gum and hence the metal part 39 is machined with a slightly overhanging portion 42 which overlies the inlay 40 in the region of the gum 38.

Figures 19, 20:
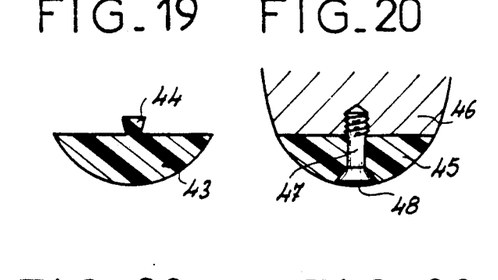
FIG. 19 illustrates an insert or facing member, in section which can be applied to the crown.
FIGS. 20 and 21 show other combinations of crowns and facing members and respective connecting techniques, also in fragmentary sections.

Inlays or coverings according to the invention can be affixed by various conventional systems to the body of the crown, these systems being machined automatically at the same time as the workpieces are trimmed by the numerically controlled machine tool. For example, when a facing member 43 is provided, it can have a dovetail tenon 44 as shown in FIG. 19 which can be machined on the pieces 43 while the complementary dovetail groove is automatically machined on the body of the crown. The facing member 45 shown in FIG. 20 is attached by a screw 47 to the metallic body 46 of the crown and a deposit or a filler 48, e.g. a ceramic cement, may cover the head of the screw.

Figure 21:
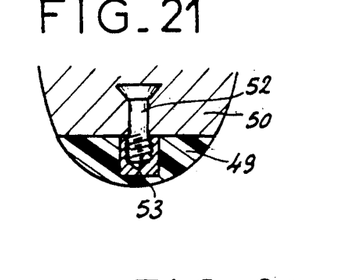

In the embodiment shown in FIG. 21, however, the facing member 59 is fixed to the metal part 50 by a screw 52 which has previously been lodged in the metal part and has its threaded portion turned toward the facing member 49 and which is received in a threaded bore 53 which may be filled with a cement for additional bonding effect.

Figure 22:
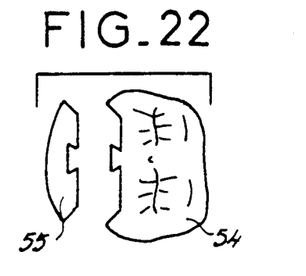
FIG. 22 illustrates in plan view the formation of a faced crown.

In FIG. 22 the metal crown 54 is provided with a recess having a dovetail projection or tenon which can be engaged by a prefabricated facing member 55 of resin or ceramic material and these two parts can be fabricated independently of one another utilizing automatic machining techniques such that the two have complementary means, namely, the tenon arrangement, for precisley fixing them together. When these two parts are joined together, therefore, the prosthesis is complete except for any final polishing which may be desired.

Figure 23:
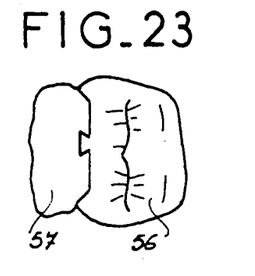
FIGS. 23 and 24 illustrate successive steps in the formation of a faced crown according to another embodiment of the invention.
Figure 24:
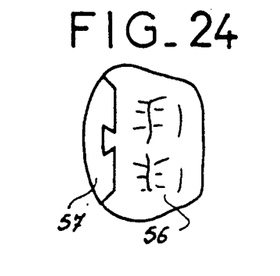

However, as illustrated in FIGS. 23 and 24, the metal part 56 of the crown may be fabricated by automatic machining in the manner described and a completely prefabricated facing member 57 may be utilized in this case. Automatic machining of the crown takes into consideration the attachment or securing system as well as the thickness of the facing piece which may ultimately be necessary while the facing piece which is prefabricated should have the maximum thickness for any type of tooth. After the facing piece 57 is secured to the crown 56 (FIG. 23) the resulting composite crown is shaped, e.g. utilizing the principles set forth in connection with FIGS. 14 and 15, thereby trimming the facing pieces 57 to the desired shape and thickness.

Figure 25:
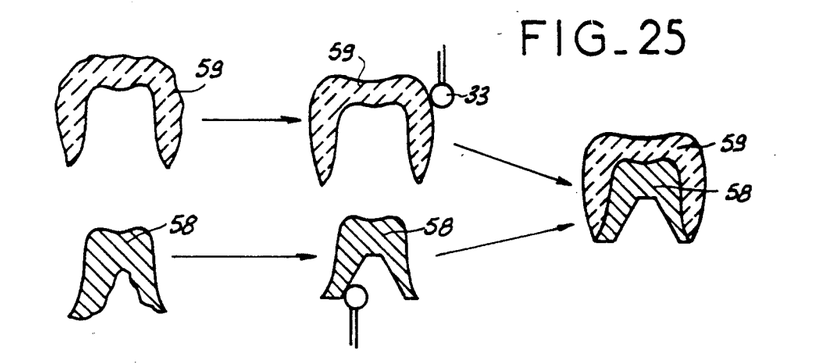
FIG. 25 is a diagram illustrating steps in the formation of still another composite crown.

For producing a ceramo-metallic crown, i.e. a crown having an inner metal base and an outer ceramic cap or covering, the technique illustrated diagrammatically in FIG. 25 may be used.

This technique may employ prefabricated metal crowns 58 and prefabricated ceramic caps 59, all of which may be stored in various sizes, shapes, and materials but such that the outer configuration of the base 58 and the inner configuration of the cap 59 are complementary to one another and are interchangeable among various bases and caps.

For a particular case, after selecting the cap and the base, utilizing the automatic machining technique, the cap 58 is milled to the configuration of the stump, e.g. the configuration of the ascertained impression or shape, while the configuration of the cap is transformed by external milling (See FIGS. 14 and 15) to correspond to the desired envelope and the occlusion. Each of these machining operations is carried out by the automatic machine tool in response to the ascertained shape and the other parameters introduced into the program or logic controlling the machine operation as described and the two parts are then cemented together as shown at the right-hand side in FIG. 25 to produce the finished crown.

Figure 26:
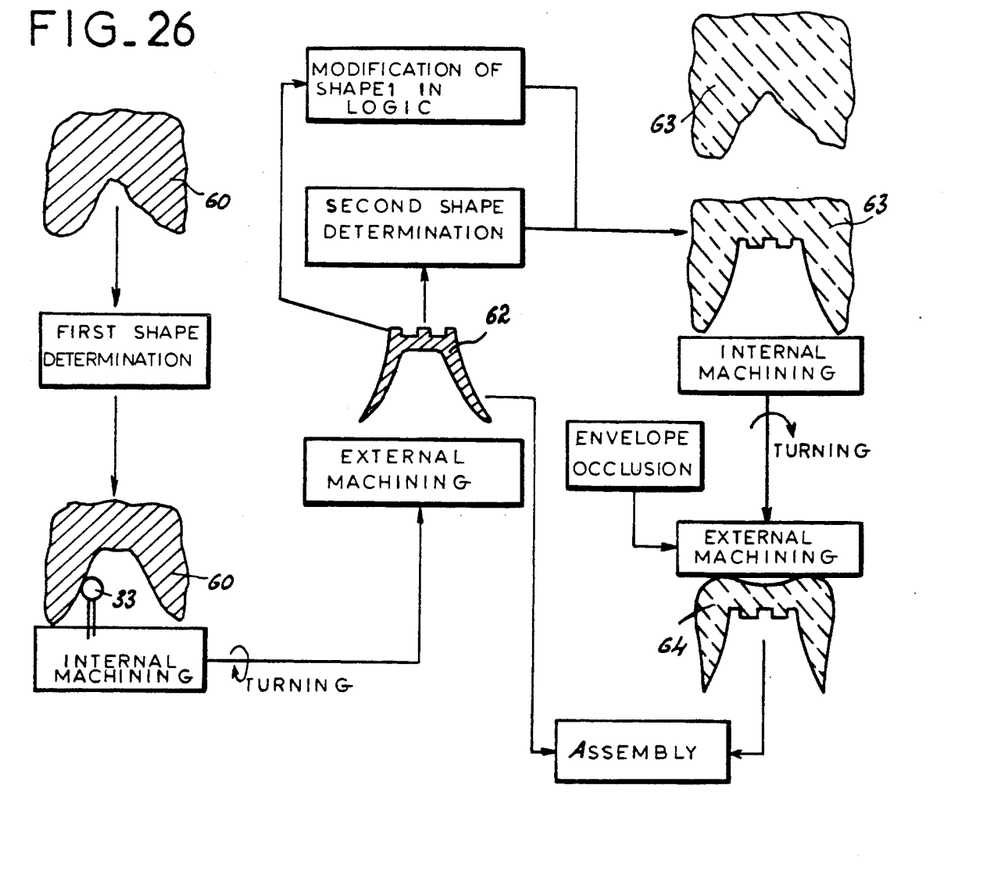
FIG. 26 is a diagram of successive steps in carrying out the method of the invention accompanied by illustrations of the various machining and other processes used.

A second method of producing a ceramo-metallic crown, according to the invention, starts from the ascertainment of the effective shape of the mouth which is realized in a metallic block 60 of metal as shown in FIG. 26. From this shape determination of the metal block is machined to provide the interior and exterior surfaces of the metal crown 62 utilizing the automatic machine tool and the milling cutter 33 as previously described. Then a second impression or shape determination is made with the crown in place and the previous determination is modified so that it now represents the taking into consideration of the thickness and shape of the metallic crown 62 and provides the basis for the internal and external machining of a ceramic block 63 to produce the outer layer or cap 64, also by automatic machining as described. The cap 64 is then assembled with the crown 62.

According to another feature of the invention, where a crown comprises a metallic support and synthetic resin facing member, a block 65 of metal may be shaped, starting with the ascertainment of the shape in the mouth, in the manner described, in a machining process in which the interior of the crown is given the configuration of the stump. This is represented at the upper left in FIG. 27. The external surface can then be simply notched as shown at 66, e.g. to provide contours for engagement of the facing which is to be subsequently formed.

Figure 27:
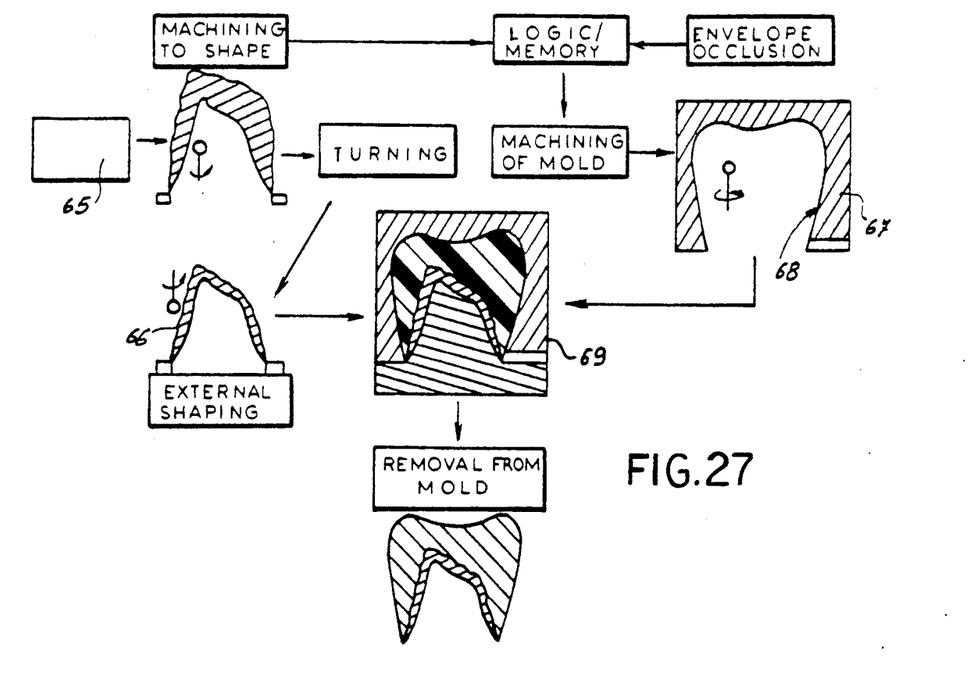
FIG. 27 is a similar diagram illustrating a composite crown fabrication process.

As a function of the envelope and the occlusion of the prosthesis to be formed, a block 67 of another material e.g. a metal, is internally machined as represented at the right-hand side of FIG. 27 utilizing the principles of this invention so as to define the external contour 68 of the crown. The metal part 66 and member 67, as thus machined, are then assembled into a mold as shown in the center of FIG. 27. The mold 69 is then supplied with a liquid material, e.g. a synthetic resin which produces the facing member and bonds it directly to the crown 66. The finished crown is shown in the lower sector of FIG. 27 after removal from the mold.

Figure 28:
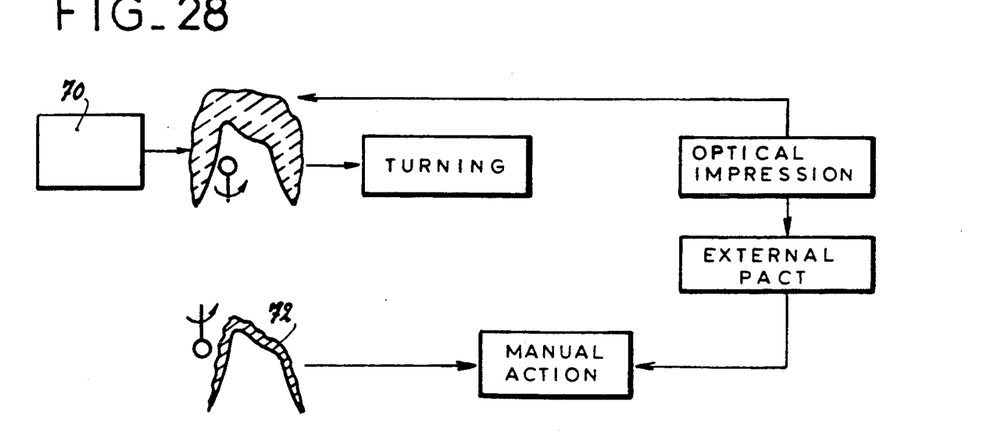
FIG. 28 is a block diagram illustrating the steps in a process according to the invention.

Still another approach is shown in FIG. 28 in which the starting block of metal 70 is automatically machined to form the internal and external surfaces thereby obtaining a metallic member 72 which has a prefabricated synthetic resin or ceramic facing applied thereto and which can be assembled to the metallic crown manually. The facing member or cap can be fabricated by conventional techniques manually or by machining techniques in the manner previously described.

Figure 29:
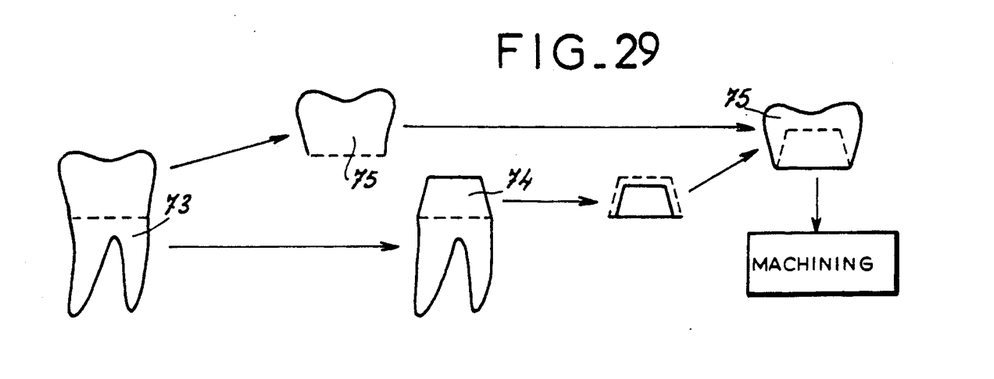
FIGS. 29 and 30 illustrate various aspects of the preparation of a crown and a dental insert according to the invention.
Figure 30:
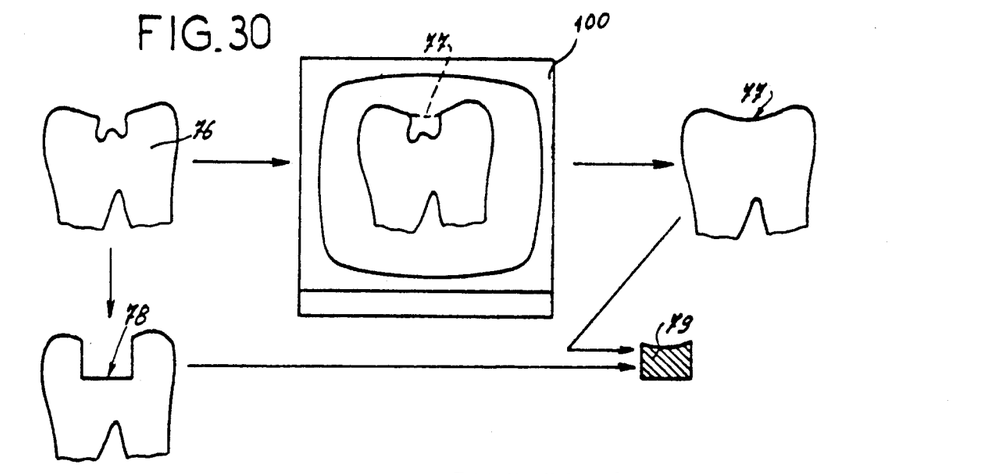

The process of the invention is also applicable in the embodiment shown in FIG. 29 to a non-damaged tooth 73 or a tooth with only slight damage (FIG. 30). In this case the impression which is originally taken to ascertain the shape is taken of the whole tooth 73 and the surrounding region and is an ascertainment of the shape befor work commences in the mouth.

Then the tooth is shaped to form a stump 74 and it may be noted that this stump can then be utilized as the basis for a second shape determination to enable the cavity of the crown to be established. After the external shape is determined by the first impression and the internal shape determined by the second impression, the composite crown shape 75 is ascertained and this is utilized automatically to fabricate the crown. Naturally, instead of a stump, a cavity can be fabricated in the existing tooth and the shape of the cavity can be utilized to determine the complementary contour of the crown which is fabricated.

During the machining process, of course, the corrections which are required are made by the calculator and computer logic circuitry, for example, to take into consideration the thickness of the cement and whether the crown is made in one piece or assembled in the manner described.

FIG. 30 illustrates the fabrication of a dental prosthesis in the form of a filling for a cavity.

After a shape determination is made from the tooth 76, the profile of the tooth is modified theoretically along the trace 77 using the monitor 100 establish the outline of the whole tooth. The region of the cavity is then excavated as shown at 78 and a further shape determination is made whereupon the calculator or computer determines the internal and external contours of the block 79 which can then be automatically machined in the manner described to fit perfectly in the excavated region of the tooth. The numerical control machine tool, which is utilized for this purpose, having its commands generated by the calculator, automatically takes into consideration any cement layer which may be required.

In a tooth suffering from greater caries damage, it is not possible to generate the shape 77 bridging the existing area with equal accuracy simply by blending the curves together. In this case, the external shape can be generated as the inverse of the actual shape of an opposing or corresponding tooth or by starting from a theoretical tooth shape.

In some cases, moreover, it may be desirable, especially to facilitate attachment of an insert, to utilize precalibrated or standard attachment techniques. In this case, the insert is machined in a blank whose bottom portion has a standard shape and size, the cavity 78 being shaped to the standard size and shape. Only the upper portion of the insert thus need be shaped by the machine tool.

Figure 31:
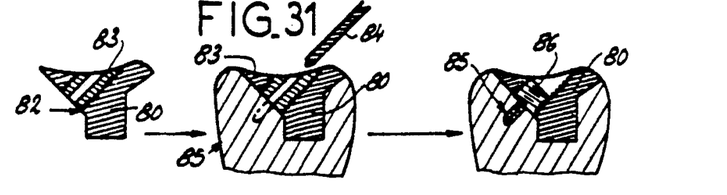
FIG. 31 is a diagram in successive sections showing the attachments of an insert according to the present invention.

FIG. 31 shows one method of attachment of such a prosthesis insert to a tooth. In this case, the prosthesis 80 is machined so as to have a threaded bore 82 of relatively large diameter which is formed automatically therein. In this threaded bore 82, there is placed a screw 83 so that it does not project beyond the surfaces of the insert. Once the insert is placed in the tooth 85a, a microdrill bit 84 guided in the axial passage of the screw 83 is used to drill a hole which can be threaded, the screw 83 is removed and is replaced by a solid screw 86 whose free end is threaded into the hole 85 and the remaining cavity can then be filled with a cement. The screw 86 can be placed by a screwdriver mounted in the turbine of the dentist, while the latter is driven very gently.

The process of the invention need not produce the final prosthesis and can be utilized as an intermediate stage in the production of the prosthesis or may also include intermediate steps in the production of the final prosthesis, the intermediate steps serving to provide sharp detection for verifying the precision of the envelope and occlusion of the prosthesis.

For example, the process may involve the machining of a model of the envelope with the aid of the chemically controlled machine tool, a verification in the mouth of the precision of the envelope and of the static and dynamic occlusions, possible retouching of the model and then a shape determination which can be utilized as the basis for the fabrication of the prosthesis itself.

In another mode of operation, a roughing out of the prosthesis can be effected by the numerical control machine tool and the roughed-out prosthesis can be inserted in the mouth for determination of the exact envelope and the particular static and dynamic occlusion characteristic with possible retouching of the roughed-out prosthesis in the mouth and final shaping of the prosthesis on the machine tool. As noted, the process can involve the storing in numerical form and in a memory. All the machining characteristics of each prosthesis are machined and placed in the mouth for possible comparision with the corresponding data for existing prostheses. This is of particular importance for basic research and for identification of corpses in forensic medicine.

From the foregoing it will be apparent that the invention provides a significant improvement over existing techniques in the production of dental prostheses, greatly increasing the speed wiht which such prostheses can be fabricated and being applicable to all prostheses no matter how complex. Indeed, it enables the fabrication of the prosthesis so that it is ready on the same day that the dentist ascertains the shape of the implantation shown. Furthermore, the final prosthesis is obtained independently of the dexterity of the dentist and his experience, it eliminates most of the manual work, much of the interventions required by individuals and eliminates possible miscommunication between the dentist and the prosthetist.

It is apparent that the invention is not limited by the embodiments described by way of explanation but also embraces all variants within the spirit and scope of the appended claims.

We claim:

1. In a process for producing a dental prosthesis for location at an implantation zone in a mouth of a subject, and in which the shape of the implantation zone is determined by talking an optical impression thereof, the improvement wherein the process comprises the steps of:

fabricating a body with a shape corresponding to the determined shape of the implantation zone at a calculator-controlled work center utilizing a calculator from a blank whose shape and material are selected by said work center, by at least one machining operation determined by the calculator and carried out by a machine tool automatically controlled to effect said operation, said machine tool constituting said work center with said calculator;

forming with said body a first part of the dental prosthesis;

assembling a second part of said prosthesis on said first part after the machining and formation of said first part; and inserting said first part into the mouth of said subject at said zone.

2. The improvement defined in claim 1 wherein said prosthesis is a prosthetic assembly of a plurality of elements in the form of an appliance, said method comprising determining the shape of said first part of the prosthesis which is to be located against the gum by developing in the logic of the calculator the surfaces of two ends of the prosthesis and a low point for the appliance.

3. The improvement defined in claim 2 which comprises determining the positions of teeth which constitute the prosthesis by first determining the appearance of the totality of an oral arcade, then determining proximal planes whose number is a function of the length of the arcade, each proximal plane being defined as a plane perpendicular to a line connecting two contact points of the prosthesis with teeth remaining in the mouth, or a point of contact and another proximal plane, then locating an array of theoretical teeth on the proximal planes, and then subjecting the array of theoretical teeth to any necessary deformation to correspond to the proper shape of the prosthesis.

4. The improvement defined in claim 3 wherein the arcade is divided into a plurality of sections which individually have a large radius of curvature based upon an angle of attack of the machine tool, then machining each section while providing the sections with a system of interconnecting them, and then interconnecting the adjacent sections.

5. The improvement defined in claim 3 wherein a support plate for teeth is provided by stamping between two parts of a mold and is then finished by a cutting operation.

6. The improvement defined in claim 2 for producing a movable prosthesis, which comprises forming two parts of a mold adapted to produce a support plate for the teeth by automatically machining the two parts of the mold starting with the determined shape of the implantation zone and utilizing a calculator program which takes into consideration the axes of insertion of the teeth, biomechanical calculations for the stability of the appliance, zones of pressure with respect to sensitive buccal areas, and hooks which must be produced to attach the prosthesis in the mouth.

7. The improvement defined in claim 6 wherein a single support plate is provided for the prosthesis and one or more prefabricated teeth are affixed to the support plate.

8. The improvement defined in claim 6 which comprises machining automatically two parts of a mold of which one corresponds to an impression of different teeth to be reproduced, the two parts of the mold being constituted of rigid material, and then injecting into the cavity between the two parts of the mold, moldable material selected from the group comprising a resin and a metal, thereby forming a support plate and the teeth which are to constitute the appliance.

9. The improvement defined in claim 8 wherein one of two parts of the mold which are machined automatically is composed of a deformable material and is shaped with cavities into which one or more prefabricated teeth are introduced, the mold in then closed and the deformable mold part is maintained by a rigid cap while said moldable material is injected into the interior of the mold to form the support plate and bonded to the prefabricated teeth lodged in the mold composed of the deformable material.

10. The improvement defined in claim 9 wherein a portion of a mold is machined corresponding to the zone from which the shape was determined and which represents not only the surface occupied by a support plate for the teeth, but that occupied by an adjoining plate zone and an adjoining lingual zone, the other mold member then being machined automatically to provide the characteristics of the support plate, the support plate is then formed by stamping and is then subjected to a cutting operation along a desired trace determined by said calculator.

11. The improvement defined in claim 1 wherein a crown base and a facing member are machined separately taking into consideration, during the machining of the crown, the thickness of the facing member and means for securing the facing member and the type of inclusion, and then the facing member is secured to the crown.

12. The improvement defined in claim 1 which comprises machining a crown based on the thickness of a facing member to be applied and means by which the facing member is to be affixed, then fixing the facing member on the crown, and thereafter machining the facing member on the crown.

13. The improvement defined in claim 1 which comprises stocking a multiplicity of metal bases and a multiplicity of prefabricated ceramic caps such that each metal base and the corresponding ceramic cap have mutually complementary external and internal contours, selecting a particular base and a particular cap from 14. The improvement defined in claim 1 wherein a metallic block is shaped to have an internal face corresponding to the determined shape and is machined externally, a new shape determination is made with the machined metal block in place in the mouth to obtain a second ascertained shape, and a ceramic block is shaped to form the cap in response to the second shape determination.

15. The improvement defined in claim 1 which comprises machining a metal block to form it internally with a configuration complementary to a stump in said zone having attachment means on an external face as a function of the envelope and the occlusion of the prosthesis to be fabricated, machining a cavity in a block of material having the external contour of the prosthesis to be fabricated thereby forming a mold between said blocks, and injecting a synthetic resin in spaces between said blocks to form a facing member on said support.

16. The improvement defined in claim 1 which comprises determining the shape of the zone of implantation and a substantially intact tooth before commencing shaping of the tooth in the mouth, shaping the tooth, thereafter determining a second shape of said zone and machining the tooth, and machining a crown automatically based upon the two shape determinations the means for fixing the prosthesis to the tooth and by superimposing the two shape determination impressions thus made.

17. The improvement defined in claim 1 wherein:

said first part is machined internally from a block of metal by said machine tool to be complementarily fitted to said implantation zone; and said first part is machined externally to complementarily receive said second part.

* * * * *